United States Patent [19]

Goldstein et al.

[11] Patent Number: 5,215,964

[45] Date of Patent: Jun. 1, 1993

[54] PEPTIDES USEFUL IN REGULATING THE IMMUNE AND NERVOUS SYSTEMS

[75] Inventors: Gideon Goldstein, Short Hills; Tapan Audhya, Bridgewater; George Heavner; Mohmed K. Anwer, both of Flemington, all of N.J.

[73] Assignee: Immunobiology Research Institute, Inc., Annandale, N.J.

[21] Appl. No.: 708,035

[22] Filed: Jun. 3, 1991

[51] Int. Cl.$^5$ .............................................. A61K 37/02
[52] U.S. Cl. ........................................ 514/17; 530/330
[58] Field of Search .......................... 530/330; 514/17

[56] References Cited

U.S. PATENT DOCUMENTS

| | | | |
|---|---|---|---|
| 4,397,842 | 8/1983 | Goldstein et al. | 424/177 |
| 4,505,853 | 3/1985 | Goldstein | 260/112.5 |

FOREIGN PATENT DOCUMENTS

| | | |
|---|---|---|
| 0410372 | 1/1991 | European Pat. Off. . |
| 263994A1 | 1/1989 | Fed. Rep. of Germany . |

OTHER PUBLICATIONS

CA 112(7): 49996z of Hoffmann et al., DD 2639941A1 (Jan. 1989).
C. M. Deber et al, Proceedings of the 11th American Peptide Symposium "Peptides", Chemistry, Structure and Biology, ed. J. E. Rivier and G. R. Marshall, pp. 585–587.
C. Grathwohl et al, Biopolymers, 20:2623–2633 (1981).
R. H. Brown et al, Brain Research, 381:237–243 (1986).
K. Venkatasubramanian et al, Proc. Natl. Acad. Sci. USA, 83:3171–3174 (1986).
M. Quik et al, Proc. Natl. Acad. Sci. USA, 88 (1991) [Quik I].
M. Quik et al, J. Neurochem., 53(4):1320–1323 (1989) [Quik II].
F. Revah et al, Proc. Natl. Acad. Sci. USA, 84:3477–3481 (1987).
M. Quik et al, J. Pharm. and Exp. Therap., 254(3):1113–1119 (1990) [Quik III].
M. Weksler et al, J. Exp. Med., 148:996–1006 (1978).
E. Sundal et al, Immune Regulation by Characterized Polypeptides, pp. 121–136 (1987).
Merrifield, Angew. Chem. Int. (ed. Engl.) 24:799–892 (1985).
Rajnavogyi et al, Chem. Abst., 105:74, Abstract No. 105:800X (1986).
Kassai Tanczos et al, Chem. Abst., 115:1053, Abstract No. 136769h (1991).
B. Noszal et al, Chem. Abst., 115:992, Abstract No. 183935u (1991).
H. Kalbacher et al, Chem. Abst., 115:1079, Abstract No. 208510s (1991).

Primary Examiner—Lester L. Lee
Assistant Examiner—Bennett M. Celsa
Attorney, Agent, or Firm—Howson and Howson

[57] ABSTRACT

Pentapeptides are disclosed which are capable of regulating the function of cells of the mammalian immune and/or nervous system. Also provided are pharmaceutical compositions containing the peptides and methods of use thereof.

21 Claims, 2 Drawing Sheets

PEPTIDES USEFUL IN REGULATING THE IMMUNE AND NERVOUS SYSTEMS

The present invention relates generally to peptides useful in the treatment of aging and abnormalities of the immune and central nervous system.

BACKGROUND OF THE INVENTION

The immunomodulatory protein thymopoietin has been isolated from bovine and human thymus. Additionally, small peptides have been chemically synthesized which mimic the biological activity of thymopoietin. See, e.g. U.S. Pat. No. 4,505,853 and corresponding EP Application No. 146,266.

A large body of articles and patents have now been published relating to such proteins and synthesized peptides. U.S. Pat. No. 4,190,646 discloses the pentapeptide thymopentin which is the active site of thymopoietin and has the sequence Arg-Lys-Asp-Val-Tyr, as well as peptide compositions in which various groups are substituted onto the amino and/or carboxyl termini of this pentapeptide.

Two distinct thymopoietin receptors (TPR) on the human T cell lines CEM and MOLT-4, have been identified. The TPR of the CEM line has been termed $\alpha$ and that of the MOLT-4 line is called $\beta$ [G. Heavner et al, *Regulatory Peptides*, 27:257–262 (1990)]. Some relationship between $\alpha$ and $\beta$ TPR activation by thymopentin and its capacity to effect changes in the immune system, particularly their activity upon lymphocytes and monocytes, have been noted.

Further, thymopoietin is known to regulate cholinergic neuromuscular transmission. [G. Goldstein et al, *Science*, 204:1309–1310 (1979) and T. Audhya et al, *Int. J. Peptide Protein Res.*, 22:568–572 (1983); M. Quik et al, *J. Neurochem.*, 53(4):1320–1323 (1989)]. This neuromuscular effect is caused by thymopoietin binding to the nicotinic acetylcholine receptor, a ligand-regulated ion channel from the vertebrate neuromuscular junction and fish electric organ, F. Revah et al, *Proc. Natl. Acad. Sci. USA*. 84:3477–3481 (1987). This constitutes a third TPR. This activity has been termed $\gamma$, and molecules capable of affecting the nicotinic acetylcholine receptor are known as being $\gamma$ positive. Thymopoietin is present within the brain, as are $\gamma$ type TPR, so that thymopoietin is almost certainly involved in brain function. $\gamma$ positive molecules are associated with activity on nerve cells, including corticotropin releasing factor (CRF) function.

More recently, thymopentin has been identified as an antagonist of stress-induced changes, exhibiting stress-protective activity [V. Klusa et al, *Regulatory Peptides*, 27:35–365 (1990)].

There remains a need in the art for additional peptides as diagnostic and/or therapeutic agents which are useful in treating dysfunctions of the immune system in mammals, including those associated with aging and various physical conditions, as well as peptides useful for treating disorders in brain functions.

SUMMARY OF THE INVENTION

The present invention describes a series of novel pentapeptides capable of regulating the function of cells of the immune and central nervous system and characterized by unusually high activity as immunomodulators in comparison to known peptides. The presence of a proline in position 4 of peptides of this invention confers upon the peptides an increased resistance to enzymes as compared to pentapeptides having similar amino acid compositions in position 1-3 and 5. Thus, the peptides of the invention have a greater in vivo potency upon oral administration as compared to the peptides of the prior art.

As one aspect, the present invention relates to novel pentapeptides having the following formula:

or a pharmaceutically acceptable acid- or base-addition salt thereof, wherein R', V, W, X, Y, and Z are as defined below in the detailed description.

As another aspect, the present invention provides methods for preparing the above-described peptides by solution synthesis, solid-phase synthesis or enzymatic synthesis.

In yet another aspect, the present invention provides pharmaceutical compositions comprising one or more of the above-identified peptides in combination with a pharmaceutically acceptable carrier.

Still a further aspect of the present invention provides methods for treating a variety of disorders and deficiencies related to the immune system, in particular, the effects of aging caused by the shrinkage of the thymus gland over time, and psychiatric disorders such as anxiety and depression, comprising administering an effective amount of a pharmaceutical composition of this invention to an affected subject.

Other aspects and advantages of the present invention are disclosed in the following detailed description containing examples of presently preferred embodiments.

DETAILED DESCRIPTION OF THE INVENTION

Figure 1:
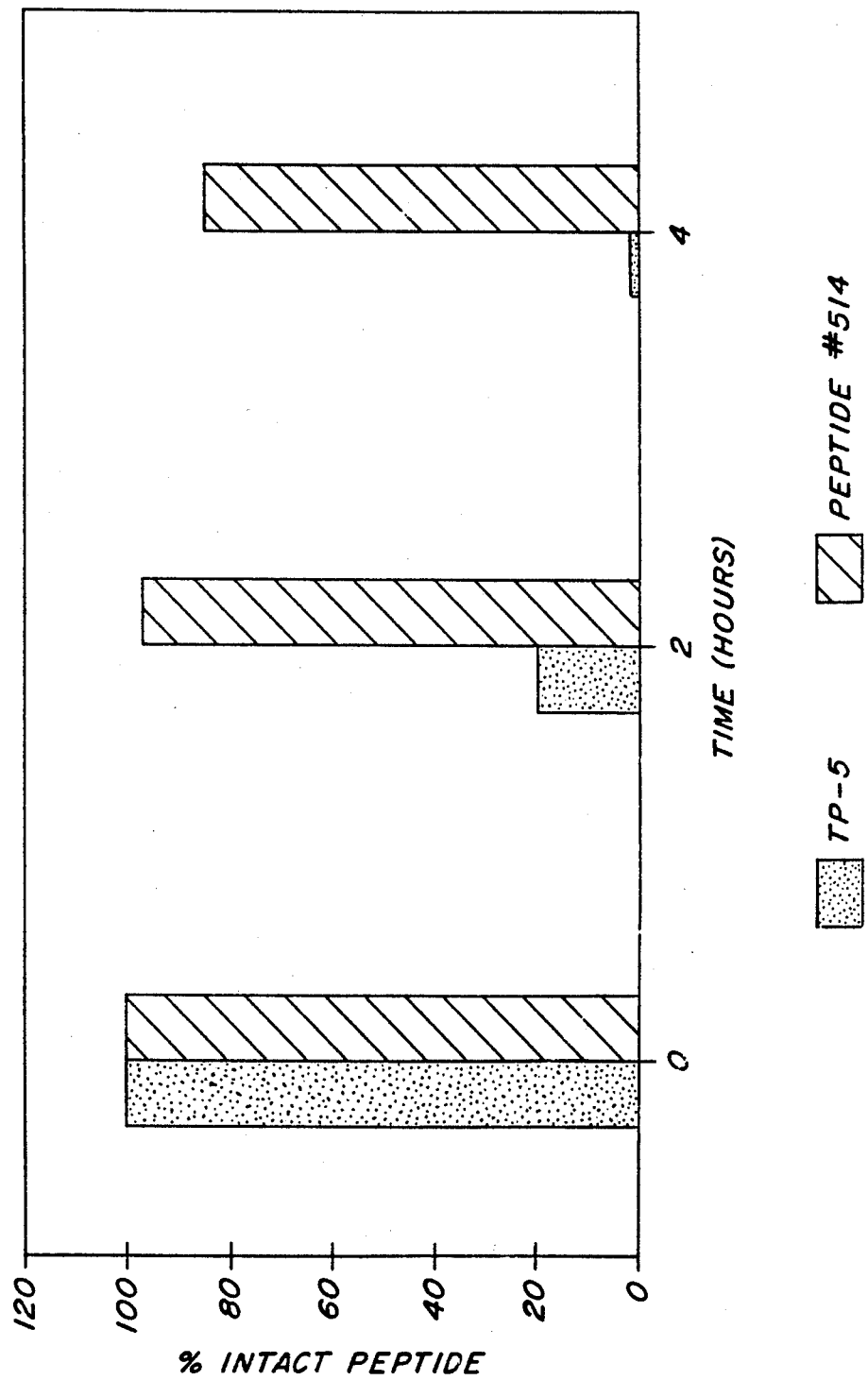
FIG. 1 is a bar graph illustrating the enzymatic stability of thymopentin and Acetyl-Arg-Pro-Asp-Pro-Phe-NH$_2$ (peptide #514) exposed to duodenum in a diffusion cell at 0, 2 and 4 hours as described in Example 17.

The present invention provides peptides capable of regulating and affecting the mammalian immune and/or central nervous system. These pentapeptides have been demonstrated to have biological activity in one or more of the following (a) CEM T cell line ($\alpha$), (b) the MOLT-4 T cell line ($\beta$), and (c) the neuromuscular assay ($\gamma$). These pentapeptides are further characterized by surprising potency in oral administration in contrast to other known peptides.

The present invention provides a series of novel pentapeptides having the following formula:

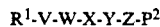

or a pharmaceutically acceptable acid- or base-addition salt thereof, wherein R$^1$ is hydrogen or a C1 to C10 lower alkyl or alkanoyl;

V is Arg;

W is Pro, dehydro-Pro or hydroxy-Pro;
X is Asp, Ser, Thr, Ala, Asn, Glu, or Gln;
Y is Pro, dehydro-Pro, or hydroxy-Pro;
Z is Phe or Tyr, optionally substituted with one or more halogen, nitro or hydroxyl group; and
$R^2$ is OH or $NP^3R^4$,
wherein $R^3$ and $R^4$ are each independently selected from the group consisting of H, a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or $R^3$ and $R^4$ together comprise a cyclic methylene group of 3 to 7 carbon atoms, and wherein optionally one of V, W, X, Y and Z is a D amino acid.

Throughout this disclosure, the amino acid components of the peptides and certain materials used in their preparation are identified by abbreviations for convenience. Most of the three letter abbreviations for amino acids are well known. As above indicated, all amino acids in the above formula are normally in the L-isomeric configuration; however in any particular peptide one amino acid may be in the D-isomeric configuration.

Peptides of these formulae, having a Pro or derivative thereof in amino acid position 2 and in amino acid position 4 are characterized by enhanced stability and resistance to attack by endo- and exopeptidases and trypsin-like enzymes in the digestive tract and in serum. This enhanced resistance to enzymatic digestion in the intestinal tract makes such peptides particularly well suited to oral administration, providing the peptides with surprising potency compared to other known peptides. Because these peptides are extremely active in oral dosages, they are especially well suited for a pharmaceutical preparation in tablet form.

One preferred pentapeptide is Acetyl-Arg-Pro-Asp-Pro-Z-NH2, where Z may be Tyr or the optionally-substituted Phe selections. A presently most preferred pentapeptide is Acetyl-Arg-Pro-Asp-Pro-Phe-NH2 [SEQ ID NO: 1]. Surprisingly, it has been found that this peptide has a potency of 10 times greater than known thymopoietin analogs. This peptide has been found to induce cGMP in both the CEM and MOLT-4 cells lines and has positive activity in the neuromuscular assay. Thus it is α, β2 and γ positive.

It has been found that the activity and the receptor specificity of this peptide can be altered by changing the amino acid in position 3. For example, if the Asp is changed to Ala, a β only peptide is created.

If Asp is substituted with Ser or Thr, an α peptide is created. To create a γ only active peptide, only Asn is substituted for Asp in the three position. Particularly preferred peptides of this invention, therefore, include:
Acetyl-Arg-Pro-Asp-Pro-Phe-NH2 [SEQ ID NO: 1]
Acetyl-Arg-Pro-Asp-Pro-Tyr-NH2 [SEQ ID NO: 2]
Acetyl-Arg-Pro-Asn-Pro-Phe-NH2 [SEQ ID NO: 3]
Acetyl-Arg-Pro-Asn-Pro-Tyr-NH2 [SEQ ID NO: 4]
Acetyl-Arg-Pro-Ala-Pro-Phe-NH2 [SEQ ID NO: 5]
Acetyl-Arg-Pro-Ala-Pro-Tyr-NH2 [SEQ ID NO: 6]
Acetyl-Arg-Pro-Glu-Pro-Tyr-NH2 [SEQ ID NO: 7]
Acetyl-Arg-Pro-Ser-Pro-Phe-NH2 [SEQ ID NO: 8]
Acetyl-Arg-Pro-Thr-Pro-Phe-NH2 [SEQ ID NO: 9]
Acetyl-Arg-Pro-Thr-Pro-Tyr-NH2 [SEQ ID NO: 10]
Acetyl-Arg-Pro-Ser-Pro-Tyr-NH2 [SEQ ID NO: 11]
Acetyl-Arg-Pro-Asp-Pro-pClPhe-NH2 [SEQ ID NO: 12]
Decanoyl-Arg-Pro-Asp-Pro-Phe-NH2 [SEQ ID NO: 13]
Acetyl-Arg-Pro-Glu-Pro-Phe-NH2 [SEQ ID NO: 14]
Acetyl-Arg-Pro-Ser-Pro-Tyr-NH2 [SEQ ID NO: 15]
Butyryl-Arg-Pro-Asn-Pro-Phe-NH2 [SEQ ID NO: 16]

Although well adapted for oral therapies, the peptides according to the invention may also be administered by any suitable route, e.g. by injection or topically. For use in topical preparations, preferably, decanoyl is substituted for acetyl because its lipophilic properties make it particularly well suited for absorption into the skin.

The peptides of this invention may generally be prepared following known techniques. Conveniently, synthetic production of the polypeptide of the invention may be according to the solid phase synthetic method described by Merrifield in J.A.C.S, 85: 2149–2154 (1963). This technique is well understood and is a common method for preparation of peptides. The solid phase method of synthesis involves the stepwise addition of protected amino acids to a growing peptide chain which is bound by covalent bonds to a solid resin particle. By this procedure, reagents and by-products are removed by filtration, thus eliminating the necessity of purifying intermediates. The general concept of this method depends on attachment of the first amino acid of the chain to a solid polymer by a covalent bond. Succeeding protected amino acids are added, one at a time (stepwise strategy), or in blocks (segment strategy), until the desired sequence is assembled. Finally, the protected peptide is removed from the solid resin support and the protecting groups are cleaved off.

The amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate, and polystyrene. Appropriate protective groups usable in such synthesis include t-butyloxycarbonyl (BOC), benzyl (BZL), t-amyloxycarbonyl (AOC), tosyl (TOS), o-bromophenylmethoxycarbonyl (BrZ), 2,6-dichlorobenzyl (BZLCl2), and phenylmethoxycarbonyl (Z or CBZ). Additional protective groups are identified in Merrifield, cited above, as well as in J. F. W. McOmie, "Protective Groups in Organic Chemistry", Plenum Press, New York, 1973. Both of these texts are incorporated herein by reference.

The general procedure of preparation of the peptides of this invention involves initially attaching the protected C-terminal amino acid to the resin. After attachment the resin is filtered, washed and the protecting group (desirably t-butyloxycarbonyl) on the alpha amino group of the C-terminal amino acid is removed. The removal of this protecting group must take place, of course, without breaking the bond between that amino acid and the resin. To the resulting resin peptide is then coupled the penultimate C-terminal protected amino acid. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Alternative techniques for peptide synthesis are described in Bodanszky et al, *Peptide Synthesis*, 2nd edition (John Wiley and Sons: 1976). For example, the peptides of the invention may also be synthesized using standard solution peptide synthesis methodologies, involving either stepwise or block coupling of amino acids or peptide fragments using chemical or enzymatic methods of amide bond formation. [See, e.g. H. D. Jakubke in *The Peptides, Analysis, Synthesis, Biology*. Academic Press (New York 1987), p. 103-165; J. D. Glass, ibid., pp. 176-184; and European Patent 0324659 A2, describing enzymatic peptide synthesis methods.] These solution synthesis methods are well known in the art.

The peptides of this invention may also be produced by other techniques known to those of skill in the art, for example, genetic engineering techniques. See, e.g., Sambrook et al, in *Molecular Cloning, a Laboratory Manual*, 2nd edition, Cold Spring Harbor Laboratory, Cold Spring Harbor, N.Y. (1989).

The acid- or base-addition salts of these peptides are also disclosed by this invention for use as diagnostic and/or therapeutic agents. Acids which are able to form salts with these peptides include, but are not limited to, inorganic acids, such as hydrochloric acid, hydrobromic acid, perchloric acid, nitric acid, thiocyanic acid, sulfuric acid, phosphoric acid, and the like. Organic acids may also be employed to form the salts of the invention, e.g., formic acid, acetic acid, propionic acid, glycolic acid, lactic acid, pyruvic acid, oxalic acid, malonic acid, succinic acid, maleic acid, fumaric acid, citric acid, succinamic acid, anthranilic acid, cinnamic acid, naphthalene sulfonic acid, sulfanilic acid, and the like.

A nonexclusive list of bases which are able to form salts with those peptides having acidic moieties includes inorganic bases, such as sodium hydroxide, ammonium hydroxide, potassium hydroxide, and the like. Organic bases for such use include, without limitation thereto, mono-, di-, and tri-alkyl and aryl amines (e.g., triethylamine, diisopropylamine, methylamine, dimethylamine) and optionally substituted ethanolamines (e.g., ethanolamine, diethanolamine).

These peptides and compositions containing these peptides surprisingly demonstrate a variety of regulatory effects on the mammalian immune and/or central nervous system. For example, these peptides of this invention offer treatment therapies for, e.g. autoimmune disorders and aging, as well as other conditions characterized by a disorder of the immune system.

Because of the immunomodulatory characteristics of the subject peptides, they are therapeutically useful in the treatment of humans, and possibly animals, since they are capable of effecting changes in the immune system of the mammal.

The significance of the ability of these peptides to bind to, and stimulate, the $\alpha$, $\beta$ or $\gamma$ receptors is related to the biological activity of the pentapeptides. The $\alpha$ and $\beta$ TPR peptides have use as modulators of the human immune system. The peptides having $\gamma$ activity have use as modulators of the human nervous system.

The peptides of the invention having $\gamma$TPR specificity may also be useful as anxiolytic therapeutic agents. For example, pretreatment of a patient with a peptide having $\gamma$ activity may reduce the levels of CRF, which mediates stress reactions. Thus, such peptides are useful as anti-depressive treatments, and similarly useful in treatment of other stress-induced disorders Also, the peptides according to the present invention may be used to diminish the effects of aging on the immune system. As the thymus shrinks with age, the level of thymopoietin, which is a thymus-derived peptide, decreases, and as a result the levels of CRF, adrenocorticotropic hormone (ACTH) and corticosteroids increase proportionally. Thus, administration of peptides of this invention which have biological activity similar to thymopoietin can help reduce the effects of aging related to inefficient or non-functioning immune systems.

The invention further provides pharmaceutical compositions containing one or more of the above-described peptides or acid- or base-addition salts thereof. The subject peptides or pharmaceutical compositions containing the peptides or their acid or basic salts are generally considered to be useful in any area in which cellular immunity is an issue and particularly where there are deficiencies in immunity.

The invention also provides a method for treatment of conditions resulting from disorder of the immune system and/or nervous system of a subject, which comprises administering to said subject a therapeutically-effective amount of at least one of the peptides or pharmaceutical compositions of this invention. For treatment of a disorder of the immune system, a therapeutically-effective amount of an $\alpha$ or $\beta$ peptide would be administered. For treatment of a disorder of the nervous system a therapeutically-effective amount of a $\gamma$ peptide would be administered. As used herein, the term "therapeutically-effective amount" means an amount which is effective to treat the conditions referred to above.

To prepare the pharmaceutical compositions of the present invention, a peptide of this invention is combined as the active ingredient in intimate admixture with a pharmaceutical carrier according to conventional pharmaceutical compounding techniques. This carrier may take a wide variety of forms depending on the form of preparation desired for administration, e.g., oral, sublingual, rectal, nasal, or parenteral.

In preparing the compositions in the preferred oral dosage form, any of the usual pharmaceutical media may be employed. For oral liquid preparations (e.g., suspensions, elixirs, and solutions), media containing, for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, and tablets). Controlled release forms may also be used. Because of their ease in administration, tablets and capsules represent the most advantageous oral dosage unit form, in which case solid pharmaceutical carriers are obviously employed. If desired, tablets may be sugar coated or enteric coated by standard techniques.

For parenteral products, the carrier will usually comprise sterile water, although other ingredients, e.g., to aid solubility or for preservation purposes may be included. Injectable suspensions may also be prepared, in which case appropriate liquid carriers, suspending agents, and the like may be employed.

A pentapeptide of the present invention is generally active when topically administered in amounts of between approximately 0.5% to about 10% by weight, and more preferably between 1-5%. See, e.g. copending U.S. Pat. application Ser. No. 07/452,757 which describes topical formulations in which peptides of this invention could be used.

A pentapeptide of the present invention is generally active when subcutaneously administered in amounts above about 0.5 mg/kg of body weight to about 10 mg/kg body weight.

These peptides are more potent orally, than subcutaneously. It is theorized that this occurs because the peptide is absorbed from the gut into the blood stream over a longer period of time, approximately 6-8 hours. During this absorbtion period about 30% of the peptide is effectively absorbed. In contrast, once in the blood stream, drugs have short half life because they are cleared and then excreted by the kidneys. Prior art peptides have been observed to have a net absorption of approximately 15%. Peptides administered subcutaneously are cleared from the body much more quickly than drugs administered orally.

The peptides of the present invention are generally active when orally administered amounts of between about 0.02 mg/kg of body weight to about 10 mg/kg of body weight, and preferably at about 0.2 mg/kg. Activity at this level makes these peptides particularly well adapted for pharmaceutical formulations in tablet size for oral administration.

The following examples are presented to illustrate the invention without specifically limiting the invention thereto. In the examples and throughout the specification, parts are by weight unless otherwise indicated. The examples employ the following abbreviations: TFA for trifluoroacetic acid; HOAc for acetic acid; $CH_2Cl_2$ for methylene chloride; $CH_3CN$ for acetonitrile; DMF for dimethyl formamide; $NH_4OAc$ for ammonium acetate; $NH_4OH$ for ammonium hydroxide; n-PrOH for n-propanol; n-BuOH for n-butanol; Pyr for pyridine; DCC for dicyclohexylcarbodiimide; HOBt for 1-hydroxybenzotriazole; DMAP for dimethylaminopyridine; HF for hydrogen fluoride; TCA for trichloroacetic acid; BHA for benzhydrylamine resin; p-MBHA for p-Methylbenzhydrylamine resin and MeOH for methanol. Other standard abbreviations can be identified by reference to *The Peptides, Analysis, Synthesis, Biology,* Vol. 1 and 2, ed. E. Gross and J. Meienhofer, Academic Press (New York 1987) and "IUPAC-IUB Commission on Biochemical Nomenclature", *J. Biol. Chem.*, 242:6489-6497 (1970) and 250:3215-3216 (1975).

EXAMPLE 1

Synthesis of Acetyl-Aro-Pro-Asp-Pro-Phe-$NH_2$ [SEQ ID NO: 1]

The pentapeptide amide was synthesized using the symmetrical anhydride coupling technique, except for arginine which was coupled via the DCC-HOBt method using the standard coupling protocols (Std 1 cycle, version 1.40) on the Applied Biosystems ABI 430A peptide synthesizer. The synthesis was initiated with 0.45 mmol of p-methylbenzhydrylamine resin.HCl (0.710 g., 0.64 mmol/g resin). The N- terminal Boc-group was removed by the end-$NH_2$ program (version 1.40). The resulting peptide was acetylated using acetic anhydride (1.0 mL) in $CH_2Cl_2$ (9 mL) containing 4-dimethylaminopyridine (15 mg) for 30 minutes. The resin was then washed with DMF($5\times10$ mL) and $CH_2Cl_2$($5\times10$ mL), and finally dried in a vacuum oven at 40° C. (1.073 g).

The peptide was cleaved from the resin support (1.07 g, 0.45 mmol) by stirring in liquid HF (10 mL), m-methylanisole (1 mL), and dimethylsulfide (1 mL) for hour at 0° C. After removal of excess HF under reduced pressure, the resin-peptide mixture was extracted with ether ($3\times50$ mL). The ether extracts were discarded. The released peptide was then extracted with 20% aqueous HOAc ($3\times33$ mL). After removal of solvents under reduced pressure, the residue obtained was dissolved in $H_2O$ (40 mL) and lyophilized (0.248 g). This solid was dissolved in $H_2O$ (10 mL) and passed through an Amberlite IRA-68 acetate form ion exchange column (60 g, 1.6 meq/mL, 2.73 cm i.d. $\times$ 18 cm length) in $H_2O$ at a flow rate of 60 mL/h. The appropriate fractions were combined and lyophilized (0.240 g).

The crude peptide (0.240 g dissolved in 4 mL of buffer "A", see below) was purified by preparative RP-HPLC using a vydac 218TP1022 column ($22\times250$ mm). The mobile phases employed were as shown below:

A=0.1% TFA/$H_2O$
B=0.1% TFA/$CH_3CN$—$H_2O$ 4.1 v/v

A linear gradient of 5% B to 23% B over 80 minutes at a flow rate of 14 mL/min. was used. The relevant fractions were combined and the organic solvents removed under reduced pressure. The aqueous residue was lyophilized (206 mg).

Thin layer chromatography was performed on Merck F-254 silica plates ($5\times10$ cm) in the following solvent systems (v/v):

Rf(1)=0.17 (1-BuOH:HOAc:$H_2O$, 4:1:1)
Rf(2)=0.47 (1-BuOH:HOAc:EtOAc:$H_2O$, 1:1:1:1)
Rf(3)=0.65 (1-BuOH:HOAc:Pyr:$H_2O$, 5:4:4:2)

Amino Acid Analysis

Arg 1.02(1), Pro 1.98(2), Asp 0.99(1), Phe 1.02(1), $NH_3$ 1.04(1).

FAB-MS: [$MH^+$] at m/z 672 a.m.u. (Mol. Wt. 671.76), where FAB-MS is Fast Atom Bombardment/Mass Spectrometry; $MH^+$ represents a positively charged mass ion; m/z is mass/charge; and a.m.u. is atomic mass units.

EXAMPLE 2

Synthesis of Acetyl-Aro-Pro-Asp-Pro-Tyr-$NH_2$ [SEQ ID NO: 2]

The pentapeptide amide was synthesized as described in Example 1, with the substitution of Tyr in the 5th position in place of Phe.

TLC: Rf(1)=0.20, Rf(2)=0.33, Rf(3)=0.85.
AAA: Arg 1.06(1), Pro 1.99(2), Asp 1.03(1), Tyr 0.92(1), $NH_3$ 1.19(1)
FAB-MS: [$MH^+$] at m/z 688 a.m.u. (Mol. Wt. 687.76).

EXAMPLE 3

Synthesis of Acetyl-Aro-Pro-Asn-Pro-Phe-$NH_2$ [SEQ ID NO: 3]

The pentapeptide amide was synthesized as described in Example 1, with the substitution of Asn for Asp in position 3. The characteristics of the peptide are as follows.

TLC: Rf(1)=0.22, Rf(2)=0.56, Rf(3)=0.72.
AAA: Arg 1.02(1), Pro 1.97(2), Asn 1.01(1), Phe 1.01(1), $NH_3$ 1.95(2).

FAB-MS: [MH+] at m/z 671 a.m.u. (Mol. Wt. 670.78).

EXAMPLE 4

Synthesis of Acetyl-Aro-Pro-Asn-Pro-Try-NH$_2$ [SEQ ID NO: 4]

The pentapeptide amide was synthesized as described in Example 1, with the substitution of Asn for Asp in position 3 and Tyr for Phe in position 5. The characteristics of the peptide are as follows.

TLC: Rf(1)=0.2, Rf(2)=0.36, Rf(3)=0.83.

AAA: Arg 1.07(1), Pro 1.98(2), Asn/Asp 1.04(1), Tyr 0.91(1), NH$_3$ 1.92(2).

FAB-MS: [MH+] at m/z 687 a.m.u. (Mol. Wt. 686.77).

EXAMPLE 5

Synthesis of Acetyl-Aro-Pro-Ala-Pro-Phe-NH$_2$ [SEQ ID NO: 5]

The pentapeptide amide was synthesized as described in Example 1, with the substitution of Ala for Asp in position 3. The characteristics of the peptide are as follows.

TLC: Rf(1)=0.18, Rf(2)=0.49, Rf(3)=0.69.

AAA: Arg 0.98(1), pro 1.97(2), Ala 1.03(1), Phe 1.02(1), NH$_3$ 1.00(1).

FAB-MS: [MH+] at m/z 628 a.m.u. (Mol Wt. 627.75).

EXAMPLE 6

Synthesis of Acetyl-Arg-Pro-Ala-Pro-Tyr-NH$_2$ [SEQ ID NO: 6]

The pentapeptide amide was synthesized as described in Example 1, with the substitution of Ala for Asp in position 3 and Tyr for Phe in position 5. The characteristics of the peptide are as follows.

TLC: Rf(1)=0.16, Rf(2)=0.32, Rf(3)=0.71.

AAA: Arg 1.04(1), Pro 1.96(2), Ala 0.99(1), Tyr 1.02(1), NH$_3$ 1.03(1).

FAB-MS: [MH+] at m/z 644 a.m.u. (Mol. Wt. 643.75).

EXAMPLE 7

Synthesis of Acetyl-Aro-Pro-Glu-Pro-Phe-NH$_2$ [SEQ ID NO: 14]

The pentapeptide amide was synthesized as described in Example 1, with the substitution of Glu for Asp in position 3. The characteristics of the peptide are as follows.

TLC: Rf(1)=0.26, Rf(2)=0.58, Rf(3)=0.74.

AAA: Arg 0.97(1), Pro 2.03(2), Glu 1.01(1), Phe 1.00(1), NH$_3$ 1.02(1).

FAB-MS: [MH+] at m/z 686 a.m.u. (Mol. Wt. 685.79).

EXAMPLE 8

Synthesis of Acetyl-Aro-Pro-Glu-Pro-Tyr-NH$_2$ [SEQ ID NO: 7]

The pentapeptide amide was synthesized as described in Example 1, with the substitution of Glu for Asp in position 3 and Tyr for Phe in position 5. The characteristics of the peptide are as follows.

TLC: Rf(1)=0.18, Rf(2)=0.35, Rf(3)=0.66.

AAA: Arg 1.02(1), Pro 1.95(2), Glu 1.03(1), Tyr 1.01(1), NH$_3$ 0.99(1).

FAB-MS: [MH+] at m/z 702 a.m.u. (Mol. Wt. 701.79).

EXAMPLE 9

Synthesis of Acetyl-Arg-Pro-Ser-Pro-Phe-NH$_2$ [SEQ ID NO: 8]

The pentapeptide amide was synthesized as described in Example 1, with the substitution of Ser for Asp in position 3. The characteristics of the peptide are as follows. TLC: Rf(1)=0.28, Rf(2)=0.62, Rf(3)=0.78.

AAA: Arg 1.01(1), Pro 2.00(2), Ser 0.62(1), Phe 0.99(1), NH$_3$ 1.16(1).

FAB-MS: [MH+] at m/z 644 a.m.u. (Mol. Wt.

EXAMPLE 10

Synthesis of Acetyl-Aro-Pro-Ser-Pro-Tyr-NH$_2$ [SEQ ID NO: 15]

The pentapeptide amide was synthesized as described in Example 1, with the substitution of Ser for Asp in position 3 and Tyr for Phe in position 5. The characteristics of the peptide are as follows.

TLC: Rf(1)=0.29, Rf(2)=0.65, Rf(3)=0.82.

AAA: Arg 1.03(1), Pro 1.95(2), Ser 0.65(1), Tyr 1.01(1), NH$_3$ 1.20(1).

FAB-MS: [MH+] at m/z 660 a.m.u. (Mol. Wt. 659.75).

EXAMPLE 11

Synthesis of Acetyl-Aro-Pro-Asp-Pro-oClPhe-NH$_2$ [SEQ ID NO: 12]

The pentapeptide amide was synthesized as described in Example 1, with the substitution of parachloro-Phe for Phe in position 5. The characteristics of the peptide are as follows.

TLC: Rf(1)=0.19, Rf(2)=0.49, Rf(3)=0.66.

AAA: Arg 1.00(1), Pro 1.99(2), Asp 0.97(1), pClPhe 1.04(1), NH$_3$ 1.02(1).

FAB-MS: [MH+] at m/z 706 a.m.u. (Mol. Wt. 706.29).

EXAMPLE 12

Synthesis of Butyryl-Aro-Pro-Asn-Pro-Phe-NH$_2$ [SEQ ID NO: 16]

The pentapeptide amide was synthesized as described in Example 1, with the substitution of Asn for Asp in position 3. The N- terminal Boc-group was removed by the end-NH2 program. The N-terminal butyryl-group was introduced by coupling with n-butyric acid using diisopropyl carbodiimide and HOBt. The characteristics of the peptide are as follows.

TLC: Rf(1)=0.32, Rf(2)=0.65, Rf(3)=0.84.

AAA: Arg 1.01(1), Pro 1.98(2), Asn 1.02(1), Phe 1.00(1), NH$_3$ 1.98(2).

FAB-MS: [MH+] at m/z 699 a.m.u. (Mol. Wt. 698.83).

EXAMPLE 13

Synthesis of Decanoyl-Aro-Pro-Asp-Pro-Phe-NH$_2$ [SEQ ID NO: 13]

The pentapeptide amide was synthesized substantially as described in Example 1, with the following modifications. The solid-phase peptide synthesis was initiated with 5 mmoles of benzhydrylamine resin and after the sequential introduction of the amino acids, the N-terminal Boc-group was removed. The resulting peptide-resin was treated with decanoic acid in DMF containing hydroxy benzotriazole and diisopropylcarbodiimide. The resin was then washed and dried (11.17 g).

The peptide was cleaved from the resin support using liquid HF as described in Example 1. The crude peptide (1.8 g), after ion-exchange, was purified by preparative RP-HPLC using the same mobile phases described in Example 1. The gradient used was 25% B to 50% B over 100 minutes at a flow rate of 14 mL/min. The yield of the pure product was 1.19 g. The characteristics of this peptide are as follows:

TLC: Rf(1)=0.30, Rf(2)=0.64, Rf(3)=0.82.

AAA: Arg 0.99(1), Pro 2.00(2), Asp 0.99(1), Phe 1.01(1), $NH_3$ 1.07(1)

FAB-MS: [MH+] at m/z 785 a.m.u. (Mol. Wt. 784.72).

EXAMPLE 14

Solution-phase Synthesis of Acetyl-Aro-Pro-Asp-Pro-Phe-$NH_2$ [SEQ ID NO: 1]

This peptide was also made by solution synthesis as described.

A. Boc-Pro-Phe-$NH_2$

To a solution of Boc-Pro-OH (4.304 g, 20 mmoles) in ethyl acetate (200 mL) at −15° C., N-methylmorpholine (2.2 mL, 20 mmoles) and isobutyl chloroformate (2.6 mL, 20 mmoles) were added. After an activation time of 10 minutes at −15° C., a solution of HCl.Phe-$NH_2$ (4.014 g, 20 mmoles) and N-methylmorpholine (2.2 mL, 20 mmoles) in dimethylacetamide (20 mL) was added. The reaction mixture was stirred at −15° C. for 30 minutes and allowed to warm to room temperature. After stirring for 2 hours at room temperature, the reaction mixture was quenched with 10% potassium carbonate solution (30 mL). The two clear layers were transferred to a separatory funnel, and the organic layer was washed successively with 10% potassium carbonate solution (2×30 mL), saturated sodium chloride solution (1×30 mL), 1N HCl (2×30 mL) and saturated sodium chloride solution (2×30 mL). After drying over anhydrous sodium sulfate, the organic solution was filtered and concentrated on a rotary evaporator under house vacuum. The product was precipitated with hexane, filtered and dried.

Yield (Theoretical): 7.229 g. Experimental Yield: 6.795 g. (94% of Theory)

B. HCl.Pro-Phe-$NH_2$

To a solution of Boc-Pro-Phe-$NH_2$ (6.506 g, 18 mmoles) in ethyl acetate (50 mL) and glacial acetic acid (25 mL), 5N HCl-ethyl acetate (20 mL) and anisole (2 mL) were added. The solution was stirred for 1 hour and concentrated on a rotary evaporator. The hydrochloride salt of the dipeptide was precipitated by the addition of ether (200 mL). The solid was filtered and dried in vacuum over KOH pellets.

C. Boc-Asp(OBzl)-Pro-Phe-$NH_2$

The mixed anhydride prepared by reacting Boc-Asp(OBzl) (5.82 g, 18 mmoles), N-methylmorpholine (1.98 mL, 18 mmoles) and isobutyl chloroformate (2.34 mL, 18 mmoles) in ethyl acetate (200 mL) at −15° C., was treated with the solution of HCl.Pro-Phe-$NH_2$ (obtained above) and N-methylmorpholine (1.98 mL, 18 mmoles) in dimethylacetamide (40 mL). The reaction was allowed to proceed for 30 minutes at −15° C. and 2 hours at room temperature. The product was worked up as described earlier and reprecipitated from ethyl acetate-hexane.

Yield (Theoretical): 10.20 g. Experimental Yield: 9.76 g (95.7% of Theory).

D. Boc-Pro-Asp(OBzl)-Pro-Phe-$NH_2$

Boc-Asp(OBzl)-Pro-Phe-$NH_2$ (9.067 g, 16 mmoles) was deprotected using HCl-ethyl acetate as described earlier and the hydrochloride salt of the tripeptide was precipitated with ether, filtered and dried.

The mixed anhydride prepared from Boc-Pro (3.44 g, 16 mmoles), N-methyl morpholine (1.76 mL, 16 mmoles) and isobutylchloroformate (2.08 mL, 16 mmoles) in ethyl acetate (160 mL) was treated with the solution of HCl.Asp(OBzl)-Pro-Phe-$NH_2$ and N-methyl morpholine (1.76 mL, 16 mmoles) in dimethylacetamide (30 mL). The reaction conditions and the product work up were described earlier. The product was crystallized from ethyl acetate-hexane.

Yield (Theoretical): 10.62 g. Experimental Yield: 10.09 g (95% of Theory).

E. Z-Arg-Pro-Asp(OBzl)-Pro-Phe-$NH_2$

Boc-Pro-Asp(OBzl)-Pro-Phe-$NH_2$ (9.96 g, 15 mmoles) was deprotected using HCl-ethyl acetate and the hydrochloride salt of the tetrapeptide was precipitated with ether, filtered and dried.

To a stirred solution of Z-Arg.HCl (5.17 g, 15 mmoles) in dimethylacetamide (25 mL) at 25° C. was added a solution of HCl.Pro-Asp(OBzl)-Pro-Phe-$NH_2$ and N-methylmorpholine (1.65 mL, 15 mmoles) in dimethylacetamide (25 mL). To the resulting solution, diethyl cyanophosphonate (2.45 g, 15 mmoles) and N-methylmorpholine (1.65 mL, 15 mmoles) were added and the mixture stirred for 4 hours. The reaction was quenched by the addition of 10% aqueous acetic acid (10 mL) and the solvents were removed on a rotary evaporator under reduced pressure. The resulting solid was triturated with 10% potassium carbonate and then with water and filtered.

Yield (Theoretical): 12.81 g. Experimental Yield: 10.25 g (80% of Theory).

F. Acetyl-Arg-Pro-Asp-Pro-Phe-$NH_2$ [SEQ ID NO: 1]

To a solution of Z-Arg-Pro-Asp(OBzl)-Pro-Phe-$NH_2$ (11.10 g, 13 mmoles) in 2-propanol (50 mL), 10% Pd on carbon (1.0 g) and saturated aqueous ammonium formate solution (2.52 g in 2 mL of water) were added with stirring. The reaction was monitored by TLC, and after 1 hour the catalyst was filtered off and the solvents were removed under reduced pressure. The residue was dissolved in water (50 mL) and freeze-dried.

Arg-Pro-Asp-Pro-Phe-$NH_2$ obtained above was dissolved in acetic acid (20 mL) and treated with acetic anhydride (6.12 g, 60 mmoles) with constant stirring. After 1 hour, the reaction was quenched by the addition of water (20 mL) and the solvents removed under reduced pressure. The residue was dissolved in water (50 mL) and freeze-dried.

The crude peptide thus obtained was purified by preparative RP-HPLC following the procedure described under Example 1. The product was lyophilized to constant weight. (Peptide content: 90%).

Yield (Theoretical): 8.73 g. Experimental Yield: 7.56 g (77.9% of Theory). The compound was indistinguishable from the product obtained in Example 1.

EXAMPLE 15

Biological Activity: Cyclic GMP Assay

A. MOLT-4 Cell Line

This assay measures the ability of a peptide of this invention to bind to the cell membrane receptor of the intact MOLT-4 cell and selectively stimulate production of cyclic GMP, as does human thymopoietin.

The MOLT-4 cell line was obtained from the American Type Culture Collection of Rockville, Md. MOLT-4 cells were freshly seeded and grown for 3 days with harvesting as described in T. Audhya et al, *Arch. Biochem Biophys.*, 234: 167–177 (1984). The cells were washed 3 times in PBS and resuspended in RPMI 1640 at a concentration of $1.0 \times b\ 10$; cells/ml and were allowed to equilibrate at 37° C. for 30 minutes before the addition of the test pentapeptides or control peptides, in 25 $\mu$l to yield a final concentration of 1, 10, and 100 $\mu$g/mL. The incubation was allowed to proceed in a shaking water bath for 4–5 minutes and was then terminated by addition of 1 ml ice-cold TCA (10 percent in $H_2O$).

The cells in TCA were homogenized and sonicated to release cyclic nucleotide. The suspension was centrifuged at $3000 \times g$ for 20 minutes at 4° C. The resulting precipitate was dissolved in 0.1N NaOH to determine the protein content. TCA was removed from the supernatant fraction by extracting 4 times with 5 ml of water-saturated diethyl ether. After the final extraction, the remaining traces of ether were removed by heating for 10 minutes in a 50° C. water bath. After lyophilization the sample was reconstituted in 50 mM acetate buffer (pH 6.2) for radioimmunoassay of cyclic GMP.

A threshold activity was determined for each peptide tested. This is defined as the lowest concentration of the test peptide which induced an intracellular level of cyclic GMP greater than two standard deviations above the control. The controls had intracellular cyclic GMP values of less than 0.5 picomoles/ml (mean±standard deviation). Test results were considered positive if the level of cyclic GMP was greater than 2 times (2 standard deviations) that determined for the parallel negative control.

The following peptides of the invention test positive for inducing increased cGMP levels in the human MOLT-4 T cell line: Acetyl-Arg-Pro-Asp-Pro-Phe-NH₂ [SEQ ID NO: 1] Acetyl-Arg-Pro-Ala-Pro-Phe-NH₂ [SEQ ID NO: 5] Acetyl-Arg-Pro-Asp-Pro-Tyr-NH₂ [SEQ ID NO: 2] Acetyl-Arg-Pro-Ala-Pro-Tyr-NH₂ [SEQ ID NO: 6] Acetyl-Arg-Pro-Glu-Pro-Tyr-NH₂ [SEQ ID NO: 7] Decanoyl-Arg-Pro-Asp-Pro-Phe-NH₂ [SEQ ID NO: 13] Butyryl-Arg-Pro-Asn-Pro-Phe-NH, [SEQ ID NO: 16]

B. CEM Cell Line

This assay measures the ability of a peptide of this invention to bind to the cell membrane receptor of the intact CEM cell and selectively stimulate production of cyclic GMP, as does human thymopoietin.

The CEM cell line was obtained from the American Type Culture Collection (Accession # ATCC CCL 119) 12301 Parklawn Drive, Rockville, Md. 20852. The cells were grown and the procedure followed is as described above for MOLT-4 cells.

The following peptides test positive for inducing increased cGMP levels in the human CEM T cell Acetyl-Arg-Pro-Asp-Pro-Phe-NH₂ [SEQ ID NO: 1] Acetyl-Arg-Pro-Ser-Pro-Phe-NH₂ [SEQ ID NO: 8] Acetyl-Arg-Pro-Thr-Pro-Phe-NH₂ [SEQ ID NO: 9] Acetyl-Arg-Pro-Asp-Pro-Tyr-NH₂ [SEQ ID NO: 2] Acetyl-Arg-Pro-Ser-Pro-Tyr-NH₂ [SEQ ID NO: 15] Acetyl-Arg-Pro-Thr-Pro-Tyr-NH₂ [SEQ ID NO: 10] Decanoyl-Arg-Pro-Asp-Pro-Phe-NH₂ [SEQ ID NO: 13] Butyryl-Arg-Pro-Asn-Pro-Phe-NH₂ [SEQ ID NO: 16] Acetyl-Arg-Pro-Asp-Pro-pClPhe-NH, [SEQ ID NO: 12]

EXAMPLE 6

Neuromuscular Assay

The neuromuscular assay is performed to determine the effect, if any, of different peptides and dosages of peptides on the γ TP receptor according to the invention. This assay is carried out as follows. Various doses of a selected peptide of this invention, prepared as described in the preceding examples, are dissolved in normal saline and injected either intravenously (i.v.) or subcutaneously (s.c.) into mice (or other selected laboratory animals). The electromyographic assay is performed according to G. Goldstein et al, *J. Jeurol. and Neurosurg. Physchiat.*, 31:453–459 (1968) 18 hours after administration of the peptide.

Mice of either sex, weighing 250–300 g, are anesthetized with 150 $\mu$l of 5% sodium pentobarbital (Abbott Laboratories, Chicago, Ill.). The nerve is stimulated with a Grass S-48 stimulator and a Grass SIV-5A stimulus isolation unit (Grass Instrument Co., Quincy, Mass.) and the electromyographic response is recorded with a Tektronix storage oscilloscope-5111 coupled to a 5A21N differential amplifier and a 5B10N time base (Tektronix, Beaverton, Oreg.).

Groups of five or more mice are used for each experiment. The threshold doses for each regimen are confirmed at least once by duplicate and fully independent experiments. The mean, standard deviation and statistical significance of differences between experimental animals and controls are assessed by one-way analysis of variance based on ratio.

The results obtained in the neuromuscular assay with a peptide according to the present invention are compared with those of thymopentin and thymopoietin. Thymopentin and thymopoietin are known to have blocking effects upon neuromuscular transmission. It is theorized that this blocking ability is enabled by interaction with the nicotinic acetylcholine receptor, designated herein as γ activity.

The following peptides according to the present invention display thymopoietin/thymopentin-like results on the neuromuscular assay and are thus designated γ-positive: Acetyl-Arg-Pro-Asp-Pro-Phe-NH₂ [SEQ ID NO: 1] Acetyl-Arg-Pro-Asn-Pro-Phe-NH₂ [SEQ ID NO: 3] Acetyl-Arg-Pro-Asp-Pro-Tyr-NH₂ [SEQ ID NO: 2] Acetyl-Arg-Pro-Asn-Pro-Tyr-NH₂ [SEQ ID NO: 4] Decanoyl-Arg-Pro-Asp-Pro-Phe-NH₂ [SEQ ID NO: 13]

EXAMPLE 17

Enzymatic Stability

To illustrate the stability of a peptide of the present invention the following assay was performed. Thymopentin and the peptide Acetyl-Arg-Pro-Asp-Pro-Phe-NH₂, identified as #514, were dissolved separately in phosphate buffer (pH 5.5). A rat duodenum was opened and attached to a 3.5 mL diffusion cell [Crownglass, N.J.] with buffer in both chambers. The selected test peptide in phosphate buffer (pH 5.5) was applied to both the cells to a final concentration of 1 mg/mL, and samples were taken at 0, 2 and 4 hours. The aliquots were subjected to high performance liquid chromatography (HPLC) with ultraviolet detection at 220 nm. The solvent system for thymopentin was phosphate buffer and methanol. For peptide #514, acetonitrile and phosphate buffer were used as the solvent system.

The bar graph of FIG. 1 illustrates that at 0 hours, thymopentin (TP-5) and peptide #514 were 100% intact. After 2 hours #514 was still approximately 100% intact while only 20% of TP-5 remained intact. Finally, at 4 hours, the amount of intact peptide #514 is approximately 90%, while the amount of intact TP-5 was negligible. Furthermore, the inventors postulate that the decrease in intact peptide #514 after 4 hours may be due to absorption to duodenum tissue since no degradation peaks were detected by HPLC.

EXAMPLE 18

CRF Inhibition Assay

A. In one assay, six female adult rats per group were injected subcutaneously with phosphate buffered saline or with 1 mg/kg body weight of peptide #514. Four days later between the hours of 8:00 am and 10:00 am, individual animals were bled through retroorbital plexus just prior to, and immediately after, a ten minute ice-water stress. During the ten minute stress period individual animals were restricted to stand in plastic cages containing ice-water maintained between 4° C. and 8° C. The blood was collected in tubes containing EDTA. Plasma was separated and corticotropin releasing factor (CRF) in the plasma was assayed as described by T. Yokoe et al, *Endocrinology*, 123:1348-1354 (1988).

Figure 2:
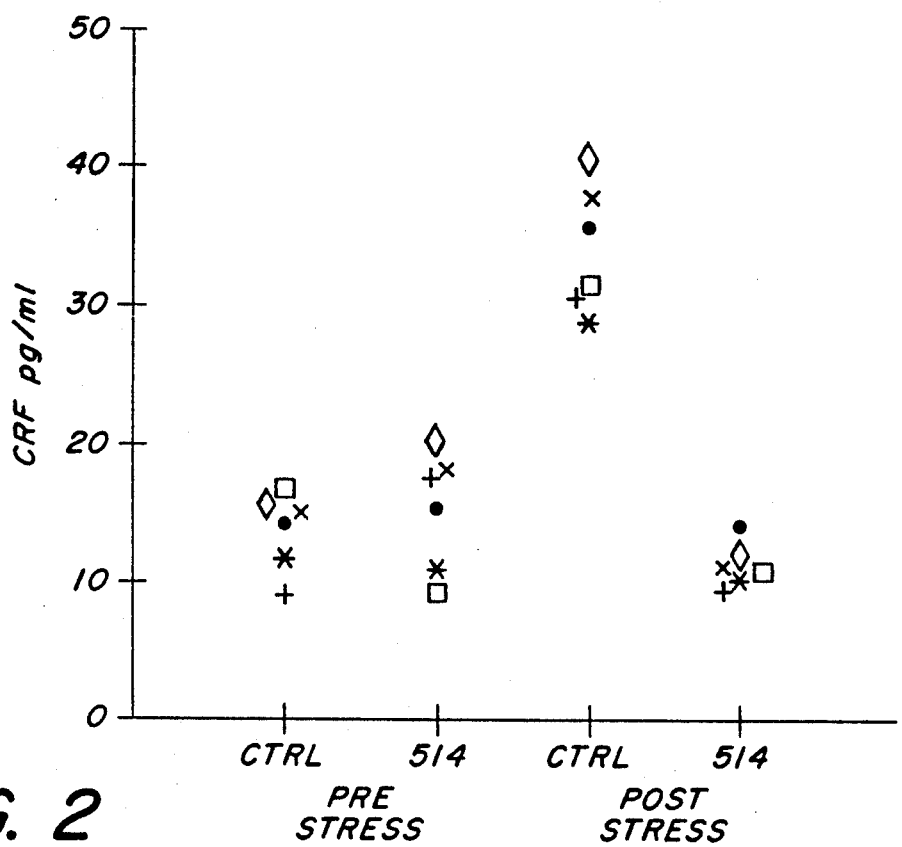
FIG. 2 is a graph of CRF levels in laboratory rats administered either a control or peptide #514 before or after exposure to a stress-inducing event as described in Example 18A.

The results of this assay are shown in FIG. 2. The symbols (diamond, X, dot, square, plus and asterisk) indicate the specific CRF levels of each rat in each group. Specifically, the recorded levels were as follows:

Control, pre-stress: 16.4, 15.3, 14.8, 14.3, 11.7 and 9.1 pg/ml;
post-stress: 31.2, 40.3, 37.8, 35.9, 28.7 and 30.6 pg/ml;

Peptide #514, pre-stress: 20.1, 18.2, 17.8, 15.2, 10.9 and 9.3 pg/ml;
post stress: 11.7, 10.2, 9.7, 14.2, 10.8 and 11.1 pg/ml.

There was no significant difference in the pre-stress CRF levels in the control animals and those treated with peptide #514. However, the post-stress CRF levels were significantly lower in the group treated with peptide #514 than those of control animals (p <0.0005).

B. In another assay, three female adult monkeys per group were injected subcutaneously with PBS or 0.1 mg/kg or 1.0 mg/kg peptide #514. Four days later, during the hours of 8:00 am and 10:00 am each animal was bled and the blood was collected in tubes containing EDTA. Plasma was separated and CRF in the plasma was assayed as described in T. Yokoe et al, cited above.

Figure 3:
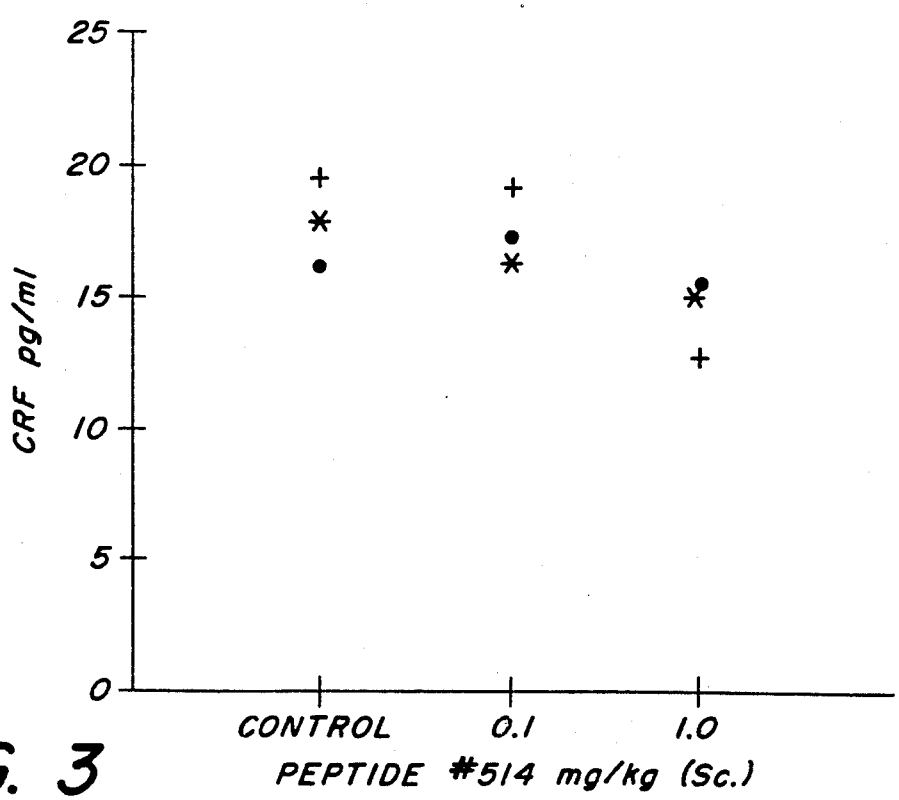
FIG. 3 is a graph of CRF levels in monkeys upon exposure to a control or to two levels of peptide #514 as described in Example 18B.

The results of this assay are shown in FIG. 3. The symbols (plus, asterisk and dot) indicate individual monkeys in each group. Specifically, control CRF levels were 19.6, 17.9 and 16.2 pg/ml; 0.1 mg/kg peptide #514 CRF levels were 19.2, 16.3 and 17.4 pg/ml; 1.0 mg/kg peptide #514 CRF levels were 15.6, 15.1 and 12.9 pg/ml. The high CRF levels indicate that the monkeys were stressed due to handling and bleeding. These "basal" values may in fact be "stressed" values. The CRF levels in the control group treated with PBS are not different from those treated with peptide #514 at a dose of 0.1 mg/kg body weight. The three monkeys treated with peptide #514 at a dose of 1.0 mg/kg body weight, however, had statistically significant lower CRF levels compared to the control group animals (p<0.05).

Numerous modifications and variations of the present invention are included in the above-identified specification and are expected to be obvious to one of skill in the art. For example, peptides other than those exemplified which fall within the above formula may be produced by a variety of methods. The peptides may be tested in the above assays without undue experimentation by one of skill in the art, given this disclosure. Such modifications and alterations to the compositions and processes of the present invention are believed to be encompassed in the scope of the claims appended hereto.

---

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Acetyl
            / note="Acetyl located on amino-terminal residue of peptide."

( i x ) FEATURE:
        ( A ) NAME/KEY: Modified-site
        ( B ) LOCATION: 5

(D) OTHER INFORMATION: /label=NH2
/ note="NH2 located on carboxy terminus of peptide."

(xi) SEQUENCE DESCRIPTION: SEQ ID NO:1:

Arg Pro Asp Pro Phe
1               5

(2) INFORMATION FOR SEQ ID NO:2:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Acetyl
/ note="Acetyl is attached to the amino terminus of the peptide."

(ix) FEATURE:
(A) NAME/KEY: Modified-site
(B) LOCATION: 5
(D) OTHER INFORMATION: /label=NH2
/ note="NH2 is attached to the carboxy terminus of the peptide."

(xi) SEQUENCE DESCRIPTION: SEQ ID NO:2:

Arg Pro Asp Pro Tyr
1               5

(2) INFORMATION FOR SEQ ID NO:3:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Acetyl
/ note="Acetyl is attached to amino terminus of peptide."

(ix) FEATURE:
(A) NAME/KEY: Modified-site
(B) LOCATION: 5
(D) OTHER INFORMATION: /label=NH2
/ note="NH2 is attached to carboxy terminus of peptide."

(xi) SEQUENCE DESCRIPTION: SEQ ID NO:3:

Arg Pro Asn Pro Phe
1               5

(2) INFORMATION FOR SEQ ID NO:4:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Acetyl -continued /note="Acetyl is attached to amino terminus of
        peptide."

( i x ) FEATURE:
        ( A ) NAME/KEY: Modified-site
        ( B ) LOCATION: 5
        ( D ) OTHER INFORMATION: /label=NH2
                /note="NH2 is attached to carboxy terminus of
                peptide."

( x i ) SEQUENCE DESCRIPTION: SEQ ID NO:4:

Arg Pro Asn Pro Tyr
1               5

( 2 ) INFORMATION FOR SEQ ID NO:5:

( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /label=Acetyl
                    /note="Acetyl is attached to amino terminus of
                    peptide."

( i x ) FEATURE:
            ( A ) NAME/KEY: Modified-site
            ( B ) LOCATION: 5
            ( D ) OTHER INFORMATION: /label=NH2
                    /note="NH2 is attached to carboxy terminus of
                    peptide."

( x i ) SEQUENCE DESCRIPTION: SEQ ID NO:5:

Arg Pro Ala Pro Phe
1               5

( 2 ) INFORMATION FOR SEQ ID NO:6:

( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /label=Acetyl
                    /note="Acetyl is attached to amino terminus of
                    peptide."

( i x ) FEATURE:
            ( A ) NAME/KEY: Modified-site
            ( B ) LOCATION: 5
            ( D ) OTHER INFORMATION: /label=NH2
                    /note="NH2 is attached to carboxy terminus of
                    peptide."

( x i ) SEQUENCE DESCRIPTION: SEQ ID NO:6:

Arg Pro Ala Pro Tyr
1               5

( 2 ) INFORMATION FOR SEQ ID NO:7:

( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /label=Acetyl
    / note="Acetyl is attached to amino terminus of peptide."

( i x ) FEATURE:
  ( A ) NAME/KEY: Modified-site
  ( B ) LOCATION: 5
  ( D ) OTHER INFORMATION: /label=NH2
    / note="NH2 is attached to carboxy terminus of peptide."

( x i ) SEQUENCE DESCRIPTION: SEQ ID NO:7:

```
Arg  Pro  Glu  Pro  Tyr
1                    5
```

( 2 ) INFORMATION FOR SEQ ID NO:8:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /label=Acetyl
    / note="Acetyl is attached to amino terminus of peptide."

( i x ) FEATURE:
  ( A ) NAME/KEY: Modified-site
  ( B ) LOCATION: 5
  ( D ) OTHER INFORMATION: /label=NH2
    / note="NH2 is attached to the carboxy terminus of the peptide."

( x i ) SEQUENCE DESCRIPTION: SEQ ID NO:8:

```
Arg  Pro  Ser  Pro  Phe
1                    5
```

( 2 ) INFORMATION FOR SEQ ID NO:9:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /label=Acetyl
    / note="Acetyl is attached to amino terminus of peptide."

( i x ) FEATURE:
  ( A ) NAME/KEY: Modified-site
  ( B ) LOCATION: 5
  ( D ) OTHER INFORMATION: /label=NH2
    / note="NH2 is attached to amino terminus of peptide."

( x i ) SEQUENCE DESCRIPTION: SEQ ID NO:9:

```
Arg  Pro  Thr  Pro  Phe
1                    5
```

( 2 ) INFORMATION FOR SEQ ID NO:10:

( i ) SEQUENCE CHARACTERISTICS:

(A) LENGTH: 5 amino acids
(B) TYPE: amino acid
(D) TOPOLOGY: linear ( i i ) MOLECULE TYPE: peptide ( i x ) FEATURE:
    (A) NAME/KEY: Modified-site
    (B) LOCATION: 1
    (D) OTHER INFORMATION: /label=Acetyl
    / note="Acetyl is attached to the amino terminus of the peptide."

( i x ) FEATURE:
    (A) NAME/KEY: Modified-site
    (B) LOCATION: 5
    (D) OTHER INFORMATION: /label=NH2
    / note="NH2 is attached to the carboxy terminus of the peptide."

( x i ) SEQUENCE DESCRIPTION: SEQ ID NO:10:

Arg Pro Thr Pro Tyr
1               5

(2) INFORMATION FOR SEQ ID NO:11:

( i ) SEQUENCE CHARACTERISTICS:
    (A) LENGTH: 5 amino acids
    (B) TYPE: amino acid
    (D) TOPOLOGY: linear ( i i ) MOLECULE TYPE: peptide ( i x ) FEATURE:
    (A) NAME/KEY: Modified-site
    (B) LOCATION: 1
    (D) OTHER INFORMATION: /label=Acetyl
    / note="Acetyl is attached to amino terminus of peptide."

( i x ) FEATURE:
    (A) NAME/KEY: Modified-site
    (B) LOCATION: 5
    (D) OTHER INFORMATION: /label=NH2
    / note="NH2 is attached to the carboxy terminus of the peptide."

( x i ) SEQUENCE DESCRIPTION: SEQ ID NO:11:

Arg Pro Ser Pro Tyr
1               5

(2) INFORMATION FOR SEQ ID NO:12:

( i ) SEQUENCE CHARACTERISTICS:
    (A) LENGTH: 5 amino acids
    (B) TYPE: amino acid
    (D) TOPOLOGY: linear ( i i ) MOLECULE TYPE: peptide ( i x ) FEATURE:
    (A) NAME/KEY: Modified-site
    (B) LOCATION: 1
    (D) OTHER INFORMATION: /label=Acetyl
    / note="Acetyl is attached to the amino terminus of the peptide."

( i x ) FEATURE:
    (A) NAME/KEY: Modified-site
    (B) LOCATION: 5
    (D) OTHER INFORMATION: /label=pClPhe-NH2
    / note="The amino acid Phe is substituted with para-Cl and NH2 is attached to the carboxy terminus of the peptide."

( x i ) SEQUENCE DESCRIPTION: SEQ ID NO:12:

Arg Pro Asp Pro Xaa (2) INFORMATION FOR SEQ ID NO:13:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Decanoyl
            / note="Decanoyl is attached to the amino terminus of the peptide."

(ix) FEATURE:
        (A) NAME/KEY: Modified-site
        (B) LOCATION: 5
        (D) OTHER INFORMATION: /label=NH2
            / note="NH2 is attached to the carboxy terminus of the peptide."

(xi) SEQUENCE DESCRIPTION: SEQ ID NO:13:

Arg  Pro  Asp  Pro  Phe
    1                      5

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Acetyl
            / note="Acetyl is attached to the amino terminus of the peptide."

(ix) FEATURE:
        (A) NAME/KEY: Modified-site
        (B) LOCATION: 5
        (D) OTHER INFORMATION: /label=NH2
            / note="NH2 is attached to the carboxy terminus of the peptide."

(xi) SEQUENCE DESCRIPTION: SEQ ID NO:14:

Arg  Pro  Glu  Pro  Phe
    1                      5

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Acetyl
            / note="Acetyl is attached to the amino terminus of the peptide."

(ix) FEATURE:
        (A) NAME/KEY: Modified-site
        (B) LOCATION: 5
        (D) OTHER INFORMATION: /label=NH2
            / note="NH2 is attached to the carboxy terminus of the peptide."

(xi) SEQUENCE DESCRIPTION: SEQ ID NO:15:

Arg Pro Ser Pro Tyr
1               5

(2) INFORMATION FOR SEQ ID NO:16:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Butyryl
            / note="Butyryl is attached to the amino terminus
            of the peptide."

(ix) FEATURE:
        (A) NAME/KEY: Modified-site
        (B) LOCATION: 5
        (D) OTHER INFORMATION: /label=NH2
            / note="NH2 is attached to carboxy terminus of the
            peptide."

(xi) SEQUENCE DESCRIPTION: SEQ ID NO:16:

Arg Pro Asn Pro Phe
1               5

We claim:

1. The pentapeptide having the formula:

$$R^1\text{-}V\text{-}W\text{-}X\text{-}Y\text{-}Z\text{-}R^2$$

or a pharmaceutically acceptable acid- or base-addition salt thereof, wherein $R^1$ is hydrogen or a C1 to C10 lower alkyl or alkanoyl;
V is Arg;
W is Pro, dehydro-Pro or hydroxy-Pro;
X is Asp, Ser, Thr, Ala, Asn, or Glu;
Y is Pro, dehydro-Pro, or hydroxy-Pro;
Z is Phe or Tyr, optionally substituted with one or more halogen, nitro or hydroxyl group; and
$R^2$ is OH or $NR^3R^4$,
    wherein $R^3$ and $R^4$ are each independently selected from the group consisting of H, a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or $R^3$ and $R^4$ together comprises a cyclic methylene group of 3 to 7 carbon atoms, and
wherein all of V, W, X, Y and Z are L-amino acids or optionally one of V, W, X, Y and Z is a D amino acid.

2. A pentapeptide selected from the group consisting of:
Acetyl-Arg-Pro-Asp-Pro-Phe-NH$_2$, SEQ ID NO: 1;
Acetyl-Arg-Pro-Asp-Pro-Tyr-NH$_2$, SEQ ID NO: 2;
Acetyl-Arg-Pro-Asn-Pro-Phe-NH$_2$, SEQ ID NO: 3;
Acetyl-Arg-Pro-Asn-Pro-Tyr-NH$_2$, SEQ ID NO: 4;
Acetyl-Arg-Pro-Ala-Pro-Phe-NH$_2$, SEQ ID NO: 5;
Acetyl-Arg-Pro-Ala-Pro-Tyr-NH$_2$, SEQ ID NO: 6;
Acetyl-Arg-Pro-Glu-Pro-Tyr-NH$_2$, SEQ ID NO: 7;
Acetyl-Arg-Pro-Ser-Pro-Phe-NH$_2$, SEQ ID NO: 8;
Acetyl-Arg-Pro-Thr-Pro-Phe-NH$_2$, SEQ ID NO: 9;
Acetyl-Arg-Pro-Thr-Pro-Tyr-NH$_2$, SEQ ID NO: 10;
Acetyl-Arg-Pro-Ser-Pro-Tyr-NH$_2$, SEQ ID NO: 11;
Acetyl-Arg-Pro-Asp-Pro-pClPhe-NH$_2$, SEQ ID NO: 12;
Decanoyl-Arg-Pro-Asp-Pro-Phe-NH$_2$, SEQ ID NO: 13;
Butyryl-Arg-Pro-Asn-Pro-Phe-NH$_2$, SEQ ID NO: 16; and
Acetyl-Arg-Pro-Glu-Pro-Phe-NH$_2$, SEQ ID NO: 14.

3. A pharmaceutical composition comprising at least one pentapeptide of claim 1 in a pharmaceutically acceptable formulation.

4. The composition according to claim 3 which is suitable for oral administration.

5. The composition according to claim 3 which is suitable for topical administration.

6. The composition according to claim 5 wherein $R^1$ is decanoyl.

7. A pentapeptide according to claim 1 having the formula Acetyl-Arg-Pro-Asp-Pro-Phe-NH$_2$, SEQ ID NO: 1.

8. A pentapeptide according to claim 1 having the formula
Acetyl-Arg-Pro-Asp-Pro-pClPhe-NH$_2$, SEQ ID NO: 12.

9. A pentapeptide according to claim 1 having the formula Decanoyl-Arg-Pro-Asp-Pro-Phe-NH$_2$, SEQ ID NO: 13.

10. A pentapeptide having the formula:

$$R^1\text{-Arg-}W\text{-Asp-}Y\text{-}Z\text{-}R^2$$

or a pharmaceutically acceptable acid- or base-addition salt thereof, wherein $R^1$ is hydrogen or a C1 to C10 lower alkyl or alkanoyl;

W is Pro, dehydro-Pro or hydroxy-Pro;
Y is Pro, dehydro-Pro, or hydroxy-Pro;
Z is Phe or Tyr, optionally substituted with one or more halogen, nitro or hydroxyl group; and
$R^2$ is OH or $NR_3R_4$, wherein $R^3$ and $R^4$ are each independently selected from the group consisting of H, a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or $R^3$ and $R^4$ together comprise a cyclic methylene group of 3 to 7 carbon atoms, and wherein all of Arg, W, Asp, Y and Z are L-amino acids or optionally one of Arg, W, Asp, Y and Z is a D amino acid.

11. A pharmaceutical composition comprising at least one pentapeptide of claim 10 in a pharmaceutically acceptable formulation.

12. A pentapeptide having the formula:

or a pharmaceutically acceptable acid- or base-addition salt thereof, wherein
$R^1$ is hydrogen or a C1 to C10 lower alkyl or alkanoyl;
W is Pro, dehydro-Pro or hydroxy-Pro;
Y is Pro, dehydro-Pro, or hydroxy-Pro;
Z is Phe or Tyr, optionally substituted with one or more halogen, nitro or hydroxyl group; and
$R^2$ is OH or $NR^3R^4$, wherein $R^3$ and $R^4$ are each independently selected from the group consisting of H, a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or $R^3$ or $R^4$ together comprise a cyclic methylene group of 3 to 7 carbon atoms, and wherein all of Arg, W, Ser, Y and Z are L-amino acids or optionally one of Arg, W, Ser, Y and Z is a D amino acid.

13. A pharmaceutical composition comprising at least one pentapeptide of claim 12 in a pharmaceutically acceptable formulation.

14. A pentapeptide having the formula:

$R^1$-Arg-W-Thr-Y-Z-$R^2$ or a pharmaceutically acceptable acid- or base-addition salt thereof, wherein
$R^1$ is hydrogen or a C1 to C10 lower alkyl or alkanoyl;
W is Pro, dehydro-Pro or hydroxy-Pro;
Y is Pro, dehydro-Pro, or hydroxy-Pro;
Z is Phe or Tyr, optionally substituted with one or more halogen, nitro or hydroxyl group; and
$R^2$ is OH or $NR^3R^4$, wherein $R^3$ and $R^4$ are each independently selected from the group consisting of H, a straight chain or branched alkyl or alkenyl having 1 to 6 carbon atoms, optionally substituted with an aryl group or aryl substituted with wither a halogen or a straight chain, a branched alkyl or alkenyl having 1 to 6 carbon atoms, or $R^3$ and $R^4$ together comprise a cyclic methylene group of 3 to 7 carbon atoms, and wherein all of Arg, W, Thr, Y and Z are L-amino acids or optionally one of Arg, W, Thr, Y and Z is a D amino acid.

15. A pharmaceutical composition comprising at least one pentapeptide of claim 14 in a pharmaceutically acceptable formulation.

16. A pentapeptide having the formula:

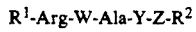

or a pharmaceutically acceptable acid- or base-addition salt thereof, wherein
$R^1$ is hydrogen or a C1 to C10 lower alkyl or alkanoyl;
W is Pro, dehydro-Pro or hydroxy-Pro;
Y is Pro, dehydro-Pro, or hydroxy-Pro;
Z is Phe or Tyr, optionally substituted with one or more halogen, nitro or hydroxyl group; and
$R^2$ is OH or $NR^3R^4$, wherein $R^3$ and $R^4$ are each independently selected from the group consisting of H, a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or $R^3$ and $R^4$ together comprises a cyclic methylene group of 3 to 7 carbon atoms, and wherein all of Arg, W, Ala, Y and Z are L-amino acids or optionally one or Arg, W, Ala, Y and Z is a D amino acid.

17. A pharmaceutical composition comprising at least one pentapeptide of claim 16 in a pharmaceutically acceptable formulation.

18. A pentapeptide having the formula:

or a pharmaceutically acceptable acid- or base-addition salt thereof, wherein
$R^1$ is hydrogen or a C1 to C10 lower alkyl or alkanoyl;
W is Pro, dehydro-Pro or hydroxy-Pro;
Y is Pro, dehydro-Pro, or hydroxy-Pro;
Z is Phe or Tyr, optionally substituted with one or more halogen, nitro or hydroxyl group; and
$R^2$ is OH or $N^3R^4$, wherein $R^3$ and $R^4$ are each independently selected from the group consisting of H, a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or $R^3$ and $R^4$ together comprise a cyclic methylene group of 3 to 7 carbon atoms; and wherein all of Arg, W, Glu, Y and Z are L-amino acids or optionally one of Arg, W, Glu, Y and Z is a D amino acid.

19. A pharmaceutical composition comprising at least one pentapeptide of claim 18 in a pharmaceutically acceptable formulation.

20. A pentapeptide having the formula:

or a pharmaceutically acceptable acid- or base-addition salt thereof, wherein
$R^1$ is hydrogen or a C1 to C10 lower alkyl or alkanoyl;
W is Pro, dehydro-Pro or hydroxy-Pro;

Y is Pro, dehydro-Pro, or hydroxy-Pro;
Z is Phe or Tyr, optionally substituted with one or more halogen, nitro or hydroxy group; and
$R^2$ is OH or $NR^3R^4$, wherein $R^3$ and $R^4$ are each independently selected from the group consisting of H, a straight chain or branched alkyl or alkenyl having 1 to 6 carbon atoms, optionally substituted with an aryl group or aryl substituted with either a halogen or a straight chain, a branched alkyl or alkenyl having 1 to 6 carbon atoms, or $R^3$ and $R^4$ together comprise a cyclic membrane group of 3 to 7 carbon atoms, and wherein all of Arg, W, Asn, Y and Z are L-amino acids or optionally one of Arg, W, Asn, Y and Z is a D amino acid.

21. A pharmaceutical composition comprising at least one pentapeptide of claim 20 in a pharmaceutically acceptable formulation.

* * * * *

UNITED STATES PATENT AND TRADEMARK OFFICE
CERTIFICATE OF CORRECTION

PATENT NO. : 5,215,964

DATED : June 1, 1993

INVENTOR(S) : Gideon Goldstein, Tapan Audhya, George Heavner, and Mohmed K. Anwer It is certified that error appears in the above-identified patent and that said Letters Patent is hereby corrected as shown below:

Col. 2, line 64, delete "$R^1-V-W-X-Y-Z-P^2$" and substitute therefor -- $R^1-V-W-X-Y-Z-R^2$ --.

Col. 3, line 6, delete "$NP^3R^4$" and substitute therefor -- $NR^3R^4$ --.

Col. 3, line 46, delete "62" and substitute therefor -- $\beta$ --.

Col. 6, line 2, after "disorders" insert -- . --.

Col. 7, line 53, in title under Example 1, delete "Aro" and substitute therefor -- Arg --.

Col. 8, line 48, in title under Example 2, delete "Aro" and substitute therefor -- Arg --.

Col. 8, line 60, in title under Example 3, delete "Aro" and substitute therefor -- Arg --.

Col. 9, line 5, in title under Example 4, delete "Aro" and substitute therefor -- Arg --.

Col. 9, line 19, in title under Example 5, delete "Aro" and substitute therefor -- Arg --.

Col. 9, line 46, in title under Example 7, delete "Aro" and substitute therefor -- Arg --.

UNITED STATES PATENT AND TRADEMARK OFFICE
CERTIFICATE OF CORRECTION

PATENT NO. : 5,215,964

DATED : June 1, 1993

INVENTOR(S) : Gideon Goldstein, Tapan Audhya, George Heavner, and Mohmed K. Anwer It is certified that error appears in the above-identified patent and that said Letters Patent is hereby corrected as shown below:

Col. 9, line 60, in title under Example 8, delete "Aro" and substitute therefor -- Arg --.

Col. 10, line 13, after "(Mol. Wt.", insert -- 643.75). --.

Col. 10, line 16, in title under Example 10, delete "Aro" and substitute therefor -- Arg --.

Col. 10, line 30, in title under Example 11, delete "Aro" and substitute therefor -- Arg --.

Col. 10, line 43, in title under Example 12, delete "Aro" and substitute therefor -- Arg --.

Col. 10, line 60, in title under Example 13, delete "Aro" and substitute therefor -- Arg --.

Col. 11, line 19, in title under Example 14, delete "Aro" and substitute therefor -- Arg --.

Col. 13, line 16, delete "1.0xb 10;" and substitute therefor -- $1.0 \times 10^7$ --.

Col. 13, line 66, after "cell", insert -- line: --.

Col. 14, line 10, delete "Example 6" and substitute therefor -- Example 16 --.

UNITED STATES PATENT AND TRADEMARK OFFICE
CERTIFICATE OF CORRECTION

PATENT NO. : 5,215,964

DATED : June 1, 1993

INVENTOR(S) : Gideon Goldstein, Tapan Audhya, George Heavner, and Mohmed K. Anwer It is certified that error appears in the above-identified patent and that said Letters Patent is hereby corrected as shown below:

Col. 14, line 22, delete "Jeurol." and substitute therefor -- Neurol. --.

Col. 29, Claim 14, line 64, delete "wither" and substitute therefor -- either --.

Signed and Sealed this

First Day of February, 1994

Attest:

BRUCE LEHMAN

Attesting Officer    Commissioner of Patents and Trademarks